(12) United States Patent
Briand et al.

(10) Patent No.: US 6,230,327 B1
(45) Date of Patent: May 15, 2001

(54) PROTECTIVE MASK FOR WELDING WITH VIEWING IN THE INFRARED AND USE OF SUCH A MASK

(75) Inventors: Francis Briand, Paris; Georges Caillibotte, Acheres, both of (FR)

(73) Assignee: La Soudure Autogene Francaise, Paris (FR)

( * ) Notice: Subject to any disclaimer, the term of this patent is extended or adjusted under 35 U.S.C. 154(b) by 0 days.

(21) Appl. No.: 09/253,714

(22) Filed: Feb. 22, 1999

(30) Foreign Application Priority Data

Mar. 12, 1998 (FR) .................................................. 98 03070

(51) Int. Cl.[7] .......................................................... A61F 9/06
(52) U.S. Cl. .......................................................... 2/8; 345/8
(58) Field of Search .................................... 2/8, 9, 422, 6.1, 2/6.2, 6.6, 6.3; 219/211; 349/11, 13, 14; 359/13, 809, 815, 630, 601, 614; 345/8; 348/373

(56) References Cited

U.S. PATENT DOCUMENTS

| | | | |
|---|---|---|---|
| 4,523,808 | | 6/1985 | Miller et al. . |
| 5,089,914 | * | 2/1992 | Prescott ................................. 359/815 |
| 5,200,827 | * | 4/1993 | Hanson et al. ........................ 358/211 |
| 5,481,622 | * | 1/1996 | Gerhardt et al. ...................... 382/103 |
| 5,515,070 | * | 5/1996 | Kawada .................................... 345/8 |
| 5,796,374 | * | 8/1998 | Cone et al. ............................... 345/8 |
| 5,812,101 | * | 9/1998 | Monarchie et al. ...................... 345/8 |
| 5,959,705 | * | 9/1999 | Fergason ................................ 349/14 |
| 6,008,780 | * | 12/1999 | Clarke et al. ............................ 345/8 |
| 6,028,627 | * | 2/2000 | Helmsderfer .......................... 348/157 |
| 6,091,546 | * | 7/2000 | Spitzer ................................... 359/618 |

FOREIGN PATENT DOCUMENTS

| | | |
|---|---|---|
| 33 14 113 | 10/1984 | (DE) . |
| 2 320 726 | 3/1977 | (FR) . |

* cited by examiner

Primary Examiner—Michael A. Neas
(74) Attorney, Agent, or Firm—Young & Thompson

(57) ABSTRACT

Protective mask which can be used in a welding operation, comprising a facial protection element, holding elements, a unit for capturing and transmitting the image, and a device for displaying the image, these being linked to the unit for capturing and transmitting the image.

12 Claims, 2 Drawing Sheets

PROTECTIVE MASK FOR WELDING WITH VIEWING IN THE INFRARED AND USE OF SUCH A MASK

FIELD OF THE INVENTION

The present invention relates to a welding helmet or mask, especially one which allows viewing in the near infrared of the welding scene.

BACKGROUND OF THE INVENTION

A welding mask usually comprises facial protection means allowing the operator's face or part of his face, to be protected from possible splashes of materials, the facial protection means being provided with holding means allowing the welding mask to be held in position on the operator's head.

The scene of the welding carried out by the operator is viewed through a window made within the facial protection means, which window is generally fitted with a tinted glass allowing the radiation emitted by the electric arc during the welding operation proper to be attenuated.

There are many grades of tinted glass allowing the light radiation to be attenuated to a greater or lesser extent, the grade to be used therefore depending on the task to be accomplished and increasing with the welding current.

Furthermore, this type of mask fitted with tinted sheets of glass therefore allows the operator, on the one hand, to see the arc and the weld pool and, on the other hand, to protect the operator from the light radiation emitted by the electric arc, namely ultraviolet, infrared and/or visible radiation.

There are also liquid-crystal helmets or masks for which the tinted glass is replaced by a cassette composed of a liquid-crystal matrix sandwiched between two polarizing sheets of glass.

These masks especially have the advantage of allowing the desired level of attenuation to be adjusted, either automatically or manually.

These two types of mask allow the operator to observe the welding scene only in the visible, i.e. from the visible radiation emitted or reflected by the welding scene.

However, in the visible spectrum, the welding arc is the main source of illumination and it follows that the radiation which emanates therefrom is predominant compared with all the other potential sources of illumination.

In other words, it is difficult to distinguish, through these conventional-type masks, anything else other than the electric arc itself and those parts of the welding scene illuminated by the electric arc, namely essentially part of the weld pool and of its immediate environment.

Thus, it is almost impossible with these masks of the prior art to distinguish the zones located near the weld pool but beneath the arc, as well as any possible transfer of material likely to occur in the electric arc itself.

SUMMARY OF THE INVENTION

The object of the present invention is therefore to remedy these drawbacks of the masks of the prior art by proposing a welding mask allowing the operator to discern, in particular, those elements of the welding scene that he could not perceive with an ordinary mask.

The present invention therefore relates to a protective mask, in particular for welding or cutting, comprising:
  facial protection means,
  holding means,
  means for capturing and transmitting at least one image, and
  means for displaying the image, these being linked to the means for capturing and transmitting the image.

It should be noted in the context of the present invention that the terms "welding mask" are employed in a general sense, i.e. they denote a protective mask capable of being used in any operation, not only a welding operation but also a cutting, thermal-spraying or similar operation.

Likewise, the terms "protective mask" and "protective helmet" are also used indiscriminately in the context of the invention.

Depending on the case, the mask of the present invention may comprise one or more of the following characteristics:
  the capture and transmission means are linked to the means for displaying at least one image via optical means;
  the means for displaying the image comprise at least one video screen, preferably at least one liquid-crystal screen;
  the means for capturing and transmitting the image comprise at least one camera, preferably a camera whose bandwidth is less than or equal to 10 $\mu$m, preferably less than or equal to 1100 nm;
  the means for capturing and transmitting the image are provided with at least one filtering means, such as a filter;
  it furthermore includes a window made within the facial protection means, the window being provided with means for attenuating the radiation in the visible;
  the means for displaying the image are linked to an optical display system which moves the image far enough away to allow the operator to see it effectively;
  the means for displaying the image are arranged on or inside the welding mask.

The invention also relates to the use of a mask according to the invention in a welding, cutting or heat-treatment process requiring the use of such a welding mask, so as to protect the operator.

BRIEF DESCRIPTION OF THE DRAWINGS

The invention will now be described in greater detail with the aid of figures which are given by way of illustration but which imply no limitation of the invention.

Figure 1:
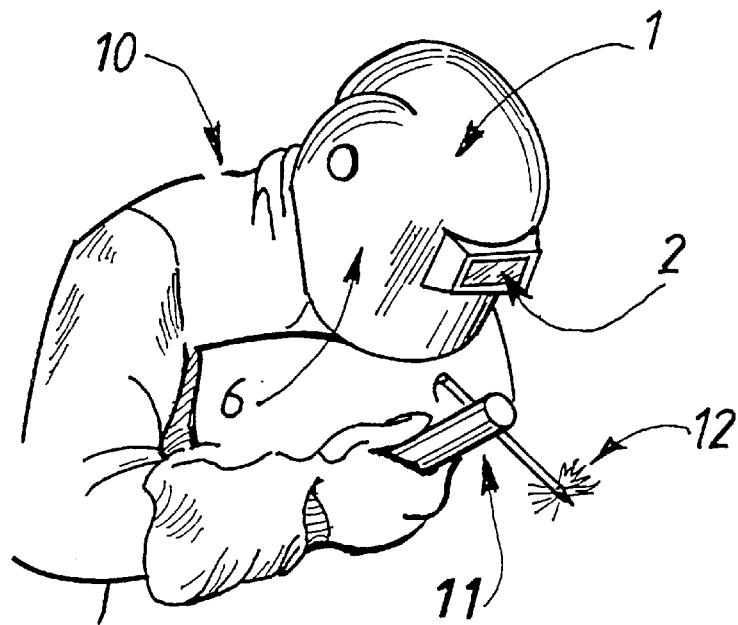
FIG. 1 shows a diagram of an operator 10 provided with a welding torch 11 producing an electric arc 12, which operator 10 is provided with a mask 1 according to the prior art, i.e. a welding mask 1 fitted with facial protection means 6 and with a window 2 provided with a tinted glass allowing some of the radiation emitted by the electric arc 12 to be attenuated.
Figure 2:
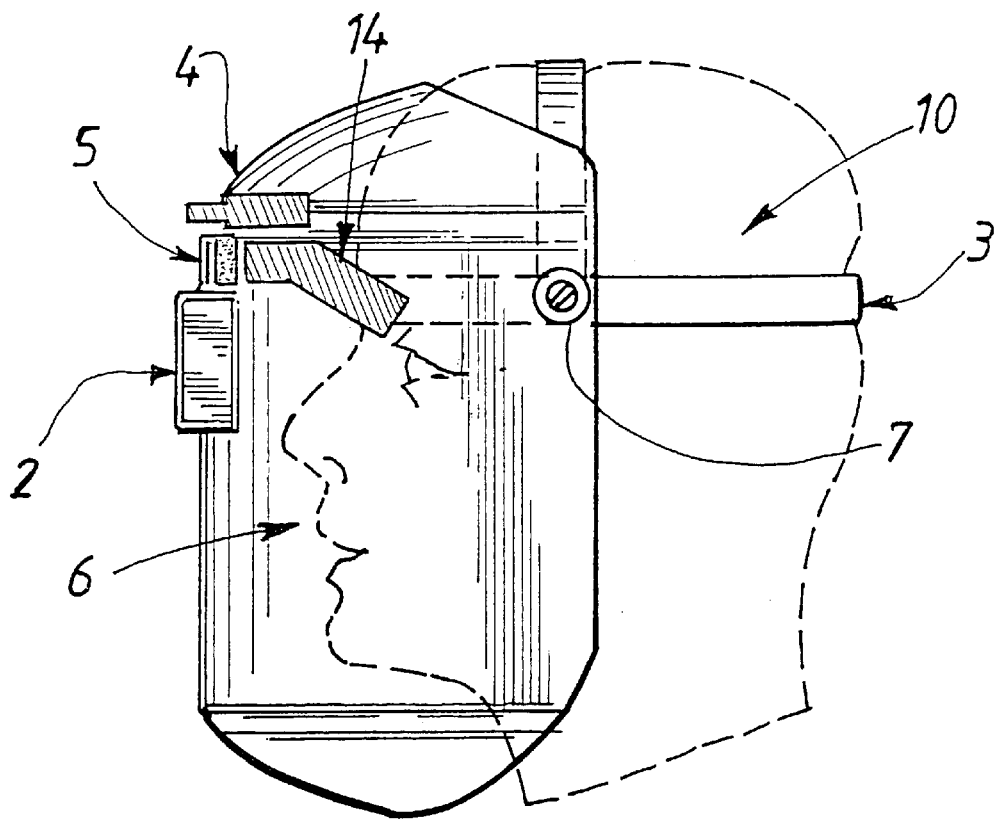
Figure 3:
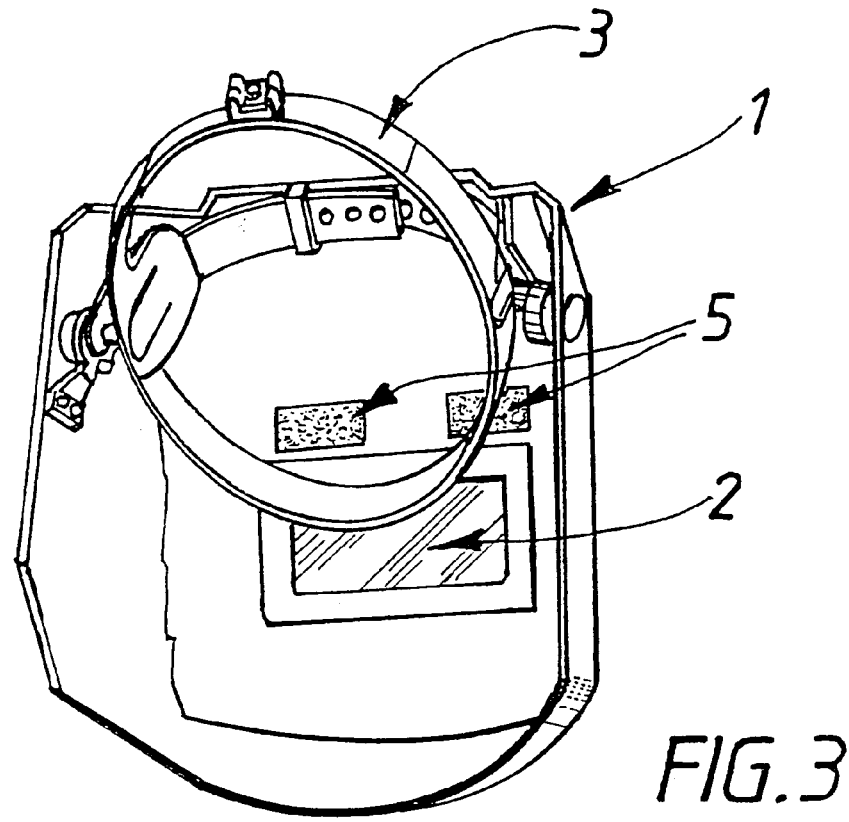
Figure 4:
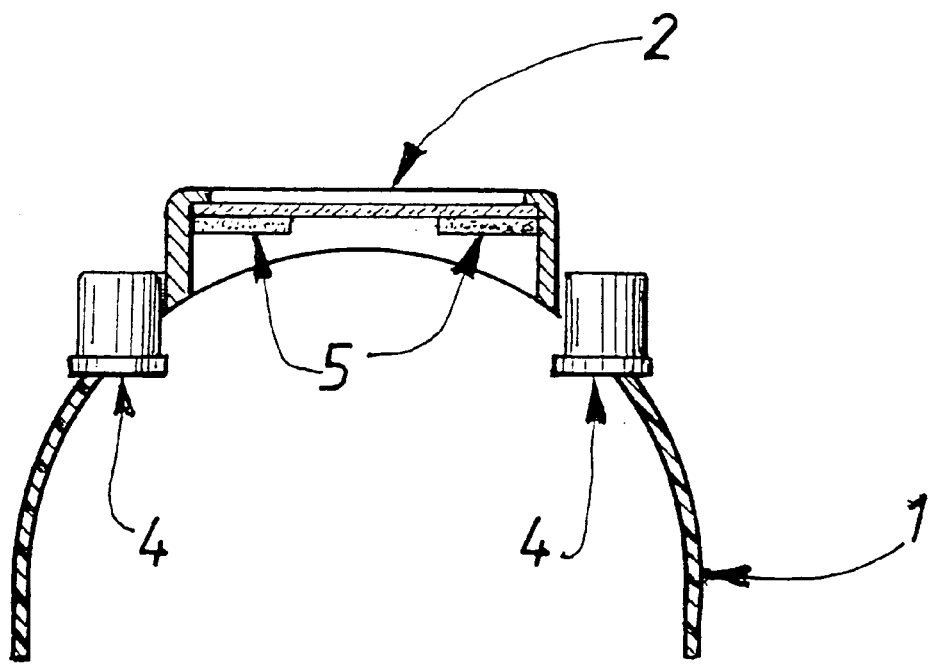

As regards FIGS. 2 to 4, these show welding masks according to the present invention.

DETAILED DESCRIPTION OF THE INVENTION

More specifically, FIG. 2 shows an operator 10 fitted with a welding mask 1 according to the present invention, which welding mask 1 is provided with holding means 3 allowing the welding mask 1 to be held in position on the head of the wearer 10.

In this case, the holding means 3 essentially comprise straps linked by screws, rivets or other similar means 7 to the facial protection means 6.

The facial protection means 6 mainly consist of a protective screen 6, for example made of plastic, to which one or more cameras 4 have been fixed, for example CCD (Charged Coupled Device) cameras linked to one or more screens 5, for example one or more liquid-crystal screens or LCD (Liquid Crystal Display) screens.

In order to allow the operator to view the screen or screens 5 effectively, it may be necessary, or even indispensable, to adjoin the screens 5 with an optical system 14 for displaying the image, such as for example a sighting system similar to those fitted on camcorders or any similar system, preferably comprising one or more lenses and capable of allowing the image to be moved sufficiently far away for it to be seen properly by the operator.

More specifically, as shown in FIGS. 2 and 3, the welding mask 1 includes, in this case, two LCD screens arranged on the inside of the welding mask 1 above a window fitted with a conventional-type tinted glass 2 or a liquid-crystal matrix.

FIG. 4 is a diagram of the arrangement of the various parts of the welding mask 1, one with respect to another.

More specifically, it may be seen in this embodiment that the welding mask 1 has two CCD cameras 4 placed on each side of and above the window fitted with a tinted pane 2 or a liquid-crystal matrix, the cameras 4 being linked to two liquid-crystal screens 5 arranged on the inside of the welding mask 1 and above the window with the tinted pane 2, as shown in FIG. 3.

The welding mask 1 according to the present invention allows the operator 10 to discern elements in the welding scene that he could not perceive with a conventional mask.

More specifically, by capturing the image of the welding scene in the near infrared, i.e. between approximately 800 and 1100 nm, the radiation from the electric arc is to a large extent obviated, thereby allowing certain sources of illumination, which hitherto were obscured, such as in particular the radiation emanating from the molten metal, to be seen.

In other words, the welding mask 1 according to the present invention allows the weld pool and any transfer of metal between the wires and the weld pool to be seen more clearly.

To achieve this, as explained above, one or more cameras 4 having a bandwidth ranging up to 1100 nm and preferably equipped with a filter allowing the visible radiation to be attenuated, for example a filter of the RG1000 type sold by the company KODAK, are therefore positioned on the welding mask 1.

The image of the welding scene captured by the cameras 4 is then transferred to one or more display screens, such as liquid-crystal screens, these being arranged on the welding mask 1, preferably inside it.

In order to allow the operator to see the welding scene properly or adequately, it may be advantageous to fit the cameras 4 with zoom and/or autofocus means, especially allowing the operator to always have a sharp picture of the welding scene when he is moving his head.

In the absence of autofocus objectives on the cameras 4, a sufficiently large depth of field of the objective, for example magnification 1, is provided so as again to maintain a sharp image when the operator is moving his head.

It is also possible to provide, on the welding mask according to the invention, means which can be disconnected as required, these means allowing the functionalities of conventional masks to be maintained, so as to be able to revert to viewing the welding scene in the visible.

The link between the cameras and the display screens is provided by a suitable optical system, in a known manner.

The welding mask according to the invention may be used in any welding operation, in particular an arc welding operation, requiring a precise and sharp picture of the entire welding scene.

In particular, the protective mask may be used in a TIG (Tungsten Inert Gas), MIG (Metal Inert Gas) or MAG (Metal Active Gas) welding operation.

What is claimed is:

1. Protective mask for welding or cutting, comprising:
   facial protection means;
   holding means;
   means for capturing and transmitting at least one image; and
   means for displaying at least one image, said means for displaying being linked to said means for capturing and transmitting the image, and comprising at least one video screen, and wherein the means for capturing and transmitting the image are provided with at least one filtering means.

2. The mask according to claim 1, wherein the means for capturing and transmitting are linked to the means for displaying the image via optical means.

3. The mask according to claim 1, wherein the video screen comprises at least one liquid-crystal screen.

4. The mask according to claim 1, wherein the means for capturing and transmitting the image comprise at least one camera.

5. The mask according to claim 4, wherein the camera has a bandwidth which is less than or equal to 10 $\mu$m.

6. The mask according to claim 5, wherein the camera has a bandwidth which is less than or equal to 1100 nm.

7. The mask according to claim 1, wherein the facial protection means includes a window, which is provided with means for attenuating visible radiation.

8. The mask according to claim 1, wherein the means for displaying the image are arranged on the welding mask.

9. The mask according to claim 1, wherein the means for displaying the image are arranged inside the welding mask.

10. The mask according to claim 1, wherein the means for displaying the image are linked to an optical display system which moves the image far enough away to allow an operator to see it effectively.

11. Method of welding, which comprises the step of welding using a protective mask having:
    facial protection means;
    holding means;
    means for capturing and transmitting at least one image; and
    means for displaying at least one image, said means for displaying being linked to said means for capturing and transmitting the image, and comprising at least one video screen.

12. Protective mask for welding or cutting, comprising:
    facial protection means;
    holding means;
    means for capturing and transmitting at least one image comprising at least one camera having a bandwidth which is less than or equal to 10 $\mu$m; and
    means for displaying at least one image, said means for displaying being linked to said means for capturing and transmitting the image, and comprising at least one video screen.

* * * * *